(12) United States Patent
Weinberg et al.

(10) Patent No.: US 9,801,608 B2
(45) Date of Patent: *Oct. 31, 2017

(54) APPARATUS AND METHOD FOR MEASURING INTRACRANIAL PRESSURE

(71) Applicant: HEADSENSE MEDICAL LTD., Netanya (IL)

(72) Inventors: Guy Weinberg, Closter, NJ (US); Surik Papyan, Haifa (IL)

(73) Assignee: HEADSENSE MEDICAL LTD., Netanya (IL)

(*) Notice: Subject to any disclaimer, the term of this patent is extended or adjusted under 35 U.S.C. 154(b) by 196 days.

This patent is subject to a terminal disclaimer.

(21) Appl. No.: 14/829,719

(22) Filed: Aug. 19, 2015

(65) Prior Publication Data

US 2015/0351716 A1 Dec. 10, 2015

Related U.S. Application Data

(63) Continuation of application No. 13/878,221, filed as application No. PCT/IL2011/000619 on Jul. 31, 2011, now Pat. No. 9,138,154.

(Continued)

(51) Int. Cl.
*A61B 8/08* (2006.01)
*A61B 5/0205* (2006.01)
(Continued)

(52) U.S. Cl.
CPC .......... *A61B 8/0808* (2013.01); *A61B 5/0205* (2013.01); *A61B 5/031* (2013.01);
(Continued)

(58) Field of Classification Search
CPC ..... A61B 5/031; A61B 8/0808; A61B 5/6817; A61B 8/461; A61B 5/0205; A61B 8/54; A61B 8/5223
(Continued)

(56) References Cited

U.S. PATENT DOCUMENTS 4,690,149 A 9/1987 Ko
4,841,986 A 6/1989 Marchbanks
(Continued)

FOREIGN PATENT DOCUMENTS

WO 98/49934 A1 11/1998
WO 99/12473 A1 3/1999
WO 2005/016121 A2 2/2005

OTHER PUBLICATIONS

Bronzino, Joseph D. (2006). Biomedical Engineering Handbook, (3rd Edition).Taylor & Francis. Ch. 1, Sect. 1, vol. 2, p. 1-2.*
(Continued)

*Primary Examiner* — David J McCrosky
(74) *Attorney, Agent, or Firm* — Chanoch Kahn; Simon Kahn

(57) ABSTRACT

An apparatus for measuring intracranial pressure constituted of: a transmitter arranged to transmit a first acoustic signal through a first cranial point; a receiver arranged to receive a second acoustic signal from a second cranial point; and a control circuitry, wherein the control circuitry is arranged to: extract from the detected second acoustic signal a first set of frequency components associated with the transmitted first acoustic signal; extract from the detected second acoustic signal a second set of frequency components associated with intracranial processes; and determine intracranial pressure responsive to the extracted first set of frequency components and the extracted second set of frequency components.

20 Claims, 4 Drawing Sheets

Related U.S. Application Data

(60) Provisional application No. 61/391,544, filed on Oct. 8, 2010.

(51) Int. Cl.
*A61B 8/00* (2006.01)
*A61B 5/03* (2006.01)
*A61B 5/00* (2006.01)

(52) U.S. Cl.
CPC ............ *A61B 5/6817* (2013.01); *A61B 8/461* (2013.01); *A61B 8/5223* (2013.01); *A61B 8/54* (2013.01)

(58) Field of Classification Search
USPC ................ 600/561, 587; 128/897, 898, 920; 702/19, 66, 75–79, 138–140
See application file for complete search history.

(56) References Cited

U.S. PATENT DOCUMENTS

| | | | |
|---|---|---|---|
| 4,971,061 A | 11/1990 | Kageyama et al. | |
| 4,984,567 A | 1/1991 | Kageyama et al. | |
| 5,074,310 A | 12/1991 | Mick | |
| 5,117,835 A | 6/1992 | Mick | |
| 5,388,583 A | 2/1995 | Ragauskas et al. | |
| 5,617,873 A | 4/1997 | Yost et al. | |
| 5,919,144 A | 7/1999 | Bridger et al. | |
| 6,117,089 A | 9/2000 | Sinha | |
| 6,387,051 B1 | 5/2002 | Ragauskas et al. | |
| 6,589,189 B2 | 7/2003 | Meyerson et al. | |
| 6,702,743 B2 | 3/2004 | Michaeli | |
| 6,773,407 B2 | 8/2004 | Yost et al. | |
| 7,104,958 B2 | 9/2006 | Crutchfield et al. | |
| 7,147,605 B2 | 12/2006 | Ragauskas | |
| 7,775,985 B2 | 8/2010 | Eide | |
| 7,850,618 B2 | 12/2010 | Wilkinson et al. | |
| 7,938,780 B2 | 5/2011 | Ragauskas et al. | |
| 8,280,502 B2 | 10/2012 | Hargrove et al. | |
| 9,138,154 B2 * | 9/2015 | Weinberg | A61B 5/031 |
| 2003/0191409 A1 | 10/2003 | Yost et al. | |
| 2006/0079773 A1 | 4/2006 | Mourad et al. | |
| 2007/0123796 A1 | 5/2007 | Lenhardt et al. | |
| 2008/0200832 A1 | 8/2008 | Stone | |
| 2010/0063405 A1 | 3/2010 | Kashif et al. | |
| 2010/0198105 A1 | 8/2010 | Avan et al. | |
| 2011/0137182 A1 | 6/2011 | Bellezza et al. | |

OTHER PUBLICATIONS

International Search Report for PCT application PCT/IL2011/00619, Issued by the EPO, dated Dec. 19, 2011.
Written Opinion of the International Searching Agency for PCT application PCT/IL2011/00619, Issued by the EPO, dated Dec. 19, 2011.
John L. Semmlow et al. "A Noninvasive Approach to Intracranial Pressure Monitoring" Journal of Clinical Engineering, 1982, vol. 7, No. 1, pp. 73-78.
Djordje Popovic et al. "Noninvasive Monitoring of Intracranial Pressure" Recent Patents on Biomedical Engineering, 2009, issue 2, pp. 165-179.
Internet Archive, Smith, "The Scientist and Engineer's Guide to Digital Signal Processing", Chapter 2, Sep. 28, 2010.
Office Action for parallel Japanese Patent Application 2013-532314 dated Mar. 17, 2015.
Office Action for parallel Russian Patent Application 2013118445/14, dated Feb. 4, 2015.
Amendment and Response to Office Action for parallel Russian Patent Application 2013118445/14, dated Feb. 4, 2015.
Office Action for parallel Russian Patent Application 2013118445/14, dated Jun. 13, 2015.
Office Action for parallel Chinese Patent Application 201180059088.9, dated Sep. 3, 2014.
Amendment and Response to Office Action for parallel Chinese Patent Application 201180059088.9, dated Sep. 3, 2014.

* cited by examiner

APPARATUS AND METHOD FOR MEASURING INTRACRANIAL PRESSURE

CROSS-REFERENCE TO RELATED APPLICATIONS

This application is a continuation of U.S. patent application Ser. No. 13/878,221 filed Apr. 7, 2013, which is a National Phase of PCT Application PCT/IL2011/000619 filed Jul. 31, 2011 entitled "APPARATUS AND METHOD FOR MEASURING INTRACRANIAL PRESSURE". PCT Application PCT/IL2011/000619 claims priority from U.S. Provisional Patent Application Ser. No. 61/391,544 filed Oct. 8, 2010 entitled "Non-invasive ICP (Intra-Cranial Pressure) monitor". The entire contents of each of the above applications are incorporated herein by reference.

TECHNICAL FIELD

The present invention relates generally to the field of non-invasive continuous intracranial pressure (ICP) monitoring.

BACKGROUND

Intracranial pressure (ICP) is the pressure within the cranium and reflects the pressure experienced by brain tissue. The body has various mechanisms by which it keeps the ICP stable, particularly by controlling cerebrospinal fluid (CSF) pressure through production and absorption of CSF. ICP is measured in millimeters of mercury (mmHg) and, at rest, is normally 7-15 mmHg for a supine adult, and becomes negative (averaging −10 mmHg) in the vertical position. Changes in ICP are attributed to volume changes in one or more of the constituents contained in the cranium.

One of the most damaging aspects of brain trauma and other head injuries is an elevated ICP. An increase in ICP, most commonly due to head injury leading to intracranial hematoma or cerebral edema, can crush brain tissue, shift brain structures, contribute to hydrocephalus, cause the brain to herniate and restrict blood supply to the brain. Additionally, it can be a cause of reflex bradycardia.

Elevated ICP reduces cerebral perfusion pressure (CPP) and if uncontrolled results in vomiting, headaches, blurred vision, or loss of consciousness. Further elevation in ICP can cause permanent brain damage and eventually a fatal hemorrhage at the base of the skull. An elevated ICP in excess of about 20 mm HG, in adults, is termed pathologic intracranial hypertension (ICH) and is considered a medical/surgical emergency. Particular instances where it is desirable to monitor ICP are in traumatic brain injury (TBI) victims, stroke victims, hydrocephalus patients, patients undergoing intracranial procedures, patients with brain tumor, "shaken baby" syndrome, kidney dialysis, or artificial liver support.

It is also possible for the ICP to drop below normal levels, though increased intracranial pressure is far more common and far more serious. The symptoms for both conditions are often the same, leading many medical experts to believe that it is the change in pressure rather than the pressure itself that results in the above symptoms.

Current ICP monitoring techniques are generally grouped as either invasive or non-invasive. The invasive group is further divided into soft tissue techniques, for example lumbar puncture, and cranial invasive techniques. The latter comprises three distinct methods for monitoring ICP:

An intraventricular catheter, which is a thin, flexible tube threaded into one of the two lateral ventricles of the brain;

A subarachnoid screw or bolt placed just through the skull in the space between the arachnoid membrane and cerebral cortex; and An epidural sensor placed into the epidural space beneath the skull.

In a lumbar puncture or spinal tap, a clinician delicately passes a fine needle through the lower region of the back into the fluid of the spinal cord. Once the spinal spaces have been penetrated, ICP can be estimated by attaching a pressure sensor. The communication between the fluid in the spinal column and the cranium allows the physician to ascertain the pressure in the cranium responsive to CSF pressure. Though invasive, a lumbar puncture is sometimes preferred because it is a soft tissue procedure rather than a cranial procedure. Generally, a non-neuro clinician will not feel comfortable performing a cranial procedure, but will perform a lumbar puncture. This procedure does allow transient manipulation or sampling of the intracranial fluid system, but is often painful and many times results in after affects, and typically raises patient apprehension. Additionally, it is a short term procedure and is generally not considered useful for long term ICP monitoring.

The cranial invasive techniques, although medically accepted and routinely used, suffer from several drawbacks. In particular, the transducer has to be calibrated in some fashion before insertion. The placement of the system requires a highly trained individual; in almost all clinical settings, this procedure is limited to physicians, and in most cases further limited to a specialist such as a neurosurgeon. This generally limits these procedures to larger medical facilities. Furthermore, there is a relatively short-term (32-72 hours) reliability and stability of the system, due to a number of causes including: leaks; plugging of the transducer; inadvertent disturbance of the transducer; or inadvertent removal of the transducer. This concern generally limits these procedures to intense monitoring setting such as an ICU. There are also associated risks of invasive transducer placement such as brain or spinal cord damage and infection. Even though these risks are low, these concerns generally limit the group of invasive ICP monitoring techniques to a hospital setting and prevents standard use of the techniques in clinic or nursing home settings.

In the non-invasive group, the accepted, commercially available method of monitoring ICP consists of taking a CT, MRI, or other image of the head, interpreting the image and observing changes in various features. This method requires a high level of skill to read and assess the images and requires that the patient be brought to the imaging equipment. In many cases, a scan is delayed or cancelled because the patient is not stable enough to be moved. Even after the patient is stable, the various tubes and equipment connections to the patient have to be accounted for during transport to the relevant imaging equipment, and as a result additional personnel may be required, with a consequent increase in cost. In addition, the scans themselves are single measurements-"snap-shots" in time, of which at least two are required to assess subtle changes and variations. A series of scans could approximate continuous monitoring, but is not economically practical.

Other methods include the estimation of the pressure using a combination of transcranial Doppler (TCD) ultrasound equipment, which is designed to assess cerebral blood flow velocities and estimation of the optic nerve sheath diameter. Such techniques are taught for example in U.S.

Patent Application Publication Ser. No. 2011/0137182 published Jun. 9, 2011 to Bellezza and Lai, the entire contents of which is incorporated herein by reference. Unfortunately, detection of optic nerve sheath diameter is difficult to perform automatically, and requires a skilled clinician to properly identify the appropriate nerve.

U.S. Pat. No. 5,919,144 issued Jul. 6, 1999 to Bridger et al., the entire contents of which is incorporated herein by reference, is addressed to a non-invasive apparatus and method for measuring ICP. An acoustic signal is transmitted through the skull of a patient and the properties of the transmitted signal after propagation through the skull are measured and correlated with ICP, particularly changes in resonant frequency response are monitored. Unfortunately, observing change in resonant frequency does not provide for a sufficiently accurate measurement of ICP. Furthermore, the technique of Bridger has not succeeded in achieving wide use after more than a decade.

U.S. patent application publication US 2008/0200832 published Aug. 21, 2008 to Stone, the entire contents of which are incorporated herein by reference, is addressed to a non-invasive ICP monitoring system and method. The system includes an auditory stimulation and recording unit which includes a stimulation controller, a memory for storing waveforms, a device for comparing waveforms with store waveforms and an alarm operable based on the comparison. The system includes at least one cranial electrode attachable to a patient, and an auditory stimulation device such as a pair of acoustic ear inserts. A patient is auditorially stimulated via the auditory stimulation device to evoke a received waveform. The received waveform is compared with an established patient baseline waveform or an established normal waveform to generate ICP information. Unfortunately, this does not provide an accurate direct measurement of ICP over a range of patients, as it is only a comparison to baseline data.

U.S. Pat. No. 6,387,051 issued May 14, 2002 to Ragauskas, the entire contents of which are incorporated herein by reference, is addressed to a to a non-invasive ICP monitoring system and method. A broadband ultrasound signal is transmitted through the skull and detected by a sensor. The received broadband signal is decomposed into narrowband components. Each component is analyzed and the ICP is determined. Unfortunately, the requirement for ultrasonic equipment adds to cost, particularly as it requires highly trained personnel for appropriate operation.

Thus, there is a long felt need for a non-invasive device operative to provide a direct measurement of ICP, providing improved accuracy and not required trained personnel.

SUMMARY

Accordingly, it is a principal object to overcome at least some of the disadvantages of prior art. This is accomplished in certain embodiments by providing an apparatus for measuring intracranial pressure comprising: a transmitter arranged to transmit a first acoustic signal through a first cranial point; a receiver arranged to receive a second acoustic signal from a second cranial point; and a control circuitry. The control circuitry is arranged to: extract from the detected second acoustic signal a first set of frequency components associated with the transmitted first acoustic signal; extract from the detected second acoustic signal a second set of frequency components associated with intracranial processes; and determine intracranial pressure responsive to the extracted first set of frequency components and the extracted second set of frequency components.

In one embodiment, the first cranial point is a first ear canal and the second cranial point is a second ear canal opposing the first ear canal. In another embodiment, the control circuitry is further arranged to output the determined intracranial pressure.

In one embodiment, the control circuitry is further arranged to: calculate a mean peak to peak value of the extracted first set of frequency components; calculate a mean of standard deviations of a plurality of windowed portions of the extracted first set of frequency components; determine a severity index responsive to the calculated mean peak to peak value and the calculated mean of standard deviations; and output an indicator of the determined severity index. In another embodiment, the control circuitry is further arranged to: calculate a mean peak to peak value of the extracted first set of frequency components; and calculate a mean of standard deviations of a plurality of windowed portions of the extracted first set of frequency components, wherein the determination of intracranial pressure by the control circuitry is responsive to the calculated mean peak to peak value and the calculated mean of standard deviations.

In one embodiment, the control circuitry is further arranged to: calculate a mean peak to peak value of the extracted second set of frequency components; and calculate a mean of standard deviations of a plurality of windowed portions of the extracted second set of frequency components, wherein the determination of intracranial pressure by the control circuitry is responsive to the calculated mean peak to peak value and the calculated mean of standard deviations. In another embodiment, the control circuitry is further arranged to: calculate a mean peak to peak value of the extracted first set of frequency components; calculate a mean of standard deviations of a plurality of windowed portions of the extracted first set of frequency components; calculate a mean peak to peak value of the extracted second set of frequency components; and calculate a mean of standard deviations of a plurality of windowed portions of the extracted second set of frequency components, wherein the determination of intracranial pressure by the control circuitry is responsive to the calculated mean peak to peak values and the calculated means of standard deviations.

In one embodiment, the control circuitry is further arranged to: calculate a mean peak to peak value of the extracted first set of frequency components; calculate a mean of standard deviations of a plurality of windowed portions of the extracted first set of frequency components; calculate a mean peak to peak value of the extracted second set of frequency components; calculate a mean of standard deviations of a plurality of windowed portions of the extracted second set of frequency components; and determine a severity index responsive to the calculated mean peak to peak value of the extracted first set of frequency components and the calculated mean of standard deviations of the extracted first set of frequency components, wherein the determination of intracranial pressure by the control circuitry is responsive to the calculated mean peak to peak values, the calculated means of standard deviations and the determined severity index. In another embodiment, the control circuitry is further arranged to: calculate the overall energy of the first set of frequency components, and wherein the intracranial pressure is determined only in the event the calculated overall energy of the first set of frequency components is greater than a predetermined minimum value.

In one embodiment, the control circuitry is further arranged to: detect amplitude values of the received second acoustic signal greater than a predetermined threshold value, and wherein the intracranial pressure is determined only in the event the number of the detected amplitude values is greater than a predetermined number. In another embodiment, the first acoustic signal exhibits a dominant frequency of less than 1000 Hz. In one further embodiment, the first acoustic signal exhibits a dominant frequency between 500-1000 Hz.

In one independent embodiment, a method for measuring intracranial pressure is provided, the method comprising: transmitting a first acoustic signal through a first cranial point; detecting a second acoustic signal from a second cranial point; extracting from the detected second acoustic signal a first set of frequency components associated with the transmitted first acoustic signal; extracting from the detected second acoustic signal a second set of frequency components associated with intracranial processes; and determining intracranial pressure responsive to the extracted first set of frequency components and the extracted second set of frequency components.

In one embodiment, the first cranial point is a first ear canal and the second cranial point is a second ear canal opposing the first ear canal. In another embodiment, the method further comprises: calculating a mean peak to peak value of the extracted first set of frequency components; calculating a mean of standard deviations of a plurality of windowed portions of the extracted first set of frequency components; determining a severity index responsive to the calculated mean peak to peak value and the calculated mean of standard deviations; and outputting an indicator of the determined severity index. In another embodiment, the method further comprises: calculating a mean peak to peak value of the extracted first set of frequency components; and calculating a mean of standard deviations of a plurality of windowed portions of the extracted first set of frequency components, wherein the determining intracranial pressure is responsive to the calculated mean peak to peak value and the calculated mean of standard deviations.

In one embodiment, the method further comprises: calculating a mean peak to peak value of the extracted second set of frequency components; and calculating a mean of standard deviations of a plurality of windowed portions of the extracted second set of frequency components, and wherein the determining intracranial pressure is responsive to the calculated mean peak to peak value and the calculated mean of standard deviation. In another embodiment, the method further comprises: calculating a mean peak to peak value of the extracted first set of frequency components; calculating a mean of standard deviations of a plurality of windowed portions of the extracted first set of frequency components; calculating a mean peak to peak value of the extracted second set of frequency components; and calculating a mean of standard deviations of a plurality of windowed portions of the extracted second set of frequency components, wherein the determining intracranial pressure is responsive to the calculated mean peak to peak values and the calculated means of standard deviations.

In one embodiment, the method further comprises: calculating a mean peak to peak value of the extracted first set of frequency components; calculating a mean of standard deviations of a plurality of windowed portions of the extracted first set of frequency components; calculating a mean peak to peak value of the extracted second set of frequency components; calculating a mean of standard deviations of a plurality of windowed portions of the extracted second set of frequency components; determining a severity index responsive to the calculated mean peak to peak value of the extracted first set of frequency components and the calculated mean of standard deviations of the extracted first set of frequency components; wherein the determining intracranial pressure is responsive to the calculated mean peak to peak values, the calculated means of standard deviations and the determined severity index. In another embodiment, the method further comprises: calculating the overall energy of the first set of frequency components, wherein the determining intracranial pressure is only in the event the calculated overall energy of the first set of frequency components is greater than a predetermined minimum value.

In one embodiment, the method further comprises: detecting amplitude values of the received second acoustic signal greater than a predetermined threshold value, wherein the determining intracranial pressure is only in the event the number of the detected amplitude values is greater than a predetermined number. In another embodiment, the transmitted first acoustic signal exhibits a dominant frequency of less than 1000 Hz. In one further embodiment, the transmitted first acoustic signal exhibits a dominant frequency between 500-1000 Hz.

Additional features and advantages will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
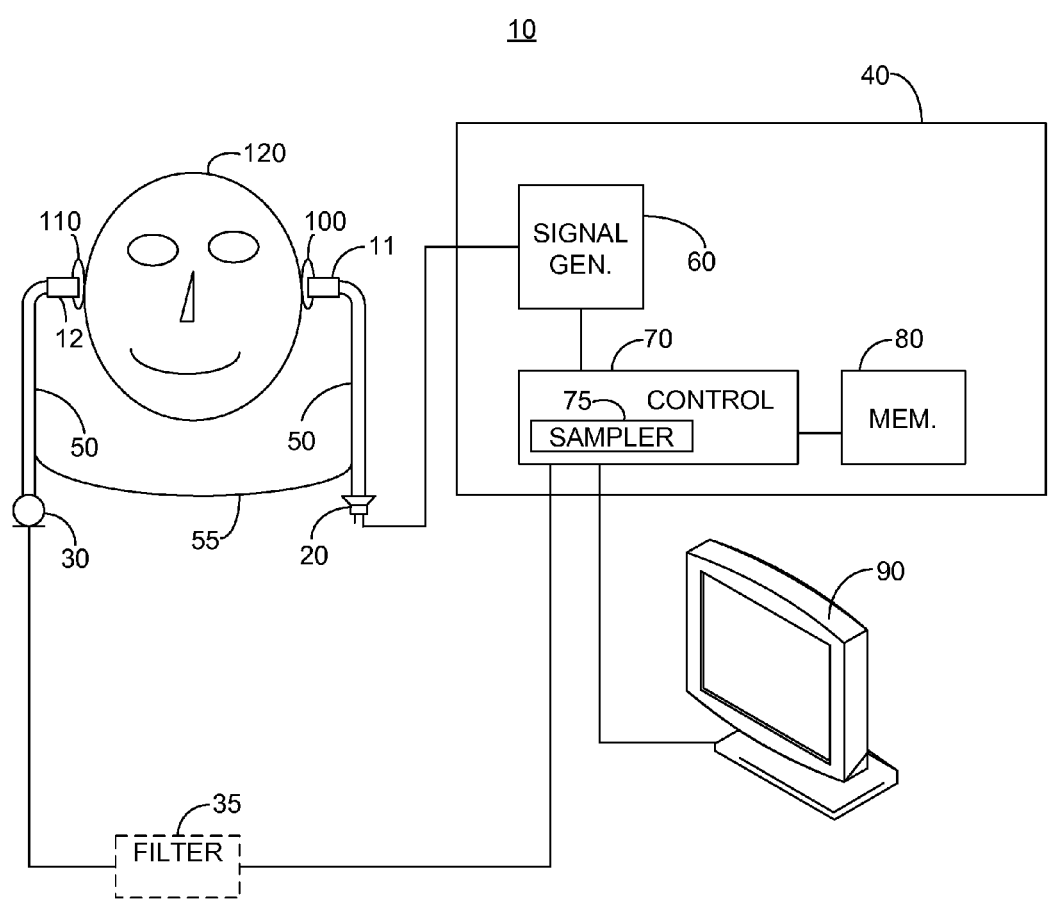
FIG. 1 illustrates a high level block diagram of a device for non-invasive measuring of ICP.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1A illustrates a high level block diagram of a device 10 for measuring ICP. Device 10 comprises: a first cranial attachment device 11; a second cranial attachment device 12; an acoustic transmitter 20; an acoustic receiver 30; an optional filter 35; a computing platform 40; a pair of tubular members 50; a connection unit 55; and a display 90. Computing platform 40 comprises: a signal generator 60; a control circuitry 70 comprising a sampler 75; a memory 80; and a display 90. In one embodiment, first cranial attachment device 11 is arranged to pass an acoustic signal with a dominant frequency between 500-1000 Hz without any substantial attenuation or distortion. In one particular embodiment first cranial attachment device 11 comprises an ear plug. In one embodiment, second cranial attachment device 12 is arranged to pass acoustic signals exhibiting frequencies of up to 1000 Hz. In one particular embodiment second cranial attachment device 12 comprises an ear plug. In one embodiment, acoustic transmitter 20 is arranged to output an acoustic signal with a dominant frequency between 500-1000 Hz without any substantial attenuation or distortion. In one embodiment, acoustic receiver 30 is a microphone. In one embodiment, acoustic receiver 30 is arranged to receive acoustic signals exhibiting frequencies of up to 1000 Hz without causing any substantial attenuation or distortion, and in particular convert the received acoustic signals of the above mentioned frequency range to an electrical signal without undue distortion. In one non-limiting embodiment, computing platform 40 is any of: a personal computer; a tablet computer; a laptop; a smartphone; and a bedside monitor. In one non-limiting embodiment, each tubular member 50 exhibits an inner diameter of about 4 mm and an outer diameter of about 5 mm. Option filter 35 is illustrated as a separate element for clarity, however this is not meant to be limiting in any way. In one embodiment, optional filter 35 is an inherent property of tubular member 50, such that acoustic receiver 30 receives a filtered acoustic signal from second cranial attachment device 12.

First cranial attachment device 11 is connected to a first end of a first tubular member 50 and acoustic transmitter 20 is connected to a second end of first tubular member 50. Second cranial attachment device 12 is connected to a first end of a second tubular member 50 and acoustic receiver 30 is connected to a second end of second tubular member 50. First cranial attachment device 11 is arranged to be attached to a first cranial point 100 of a patient head 120. In one embodiment, first cranial point 100 is a first ear canal. Second cranial attachment device 12 is arranged to be attached to a second cranial point 110 of patient head 120. In one embodiment, second cranial point 110 is a second ear canal, preferably opposing the first ear canal. In one further embodiment, each of first cranial attachment device 11 and second cranial attachment device 12 is arranged to be maintained within a respective ear canal. Acoustic signals output from acoustic transmitter 20 are arranged to propagate through first tubular member 50 and into first cranial point 100 via first cranial attachment device 11. Acoustic signals entering second cranial attachment device 12 are arranged to propagate through second tubular member 50 to be received by acoustic receiver 30. In one embodiment, connection unit 55 mechanically connects first and second tubular members to each other, such that they remain in a constant position in relation to patient head 120, and preferably further urges each of first cranial attachment device 11 and second cranial attachment device 12 towards the respective first cranial point 100 and second cranial point 110. In one non-limiting embodiment connection unit 55 comprises a pressure arch.

In another embodiment (not shown), acoustic transmitter 20 is placed within first cranial attachment device 11 and acoustic receiver 30 is place within second cranial attachment device 12. In one embodiment, each of acoustic transmitter 20 and acoustic receiver 30 is disposed within a respective portion of a single binaural device, such that acoustic transmitter 20 is arranged to transmit sound into a first ear canal via a first earpiece of the binaural device representative of first cranial attachment device 11 and acoustic receiver 30 is arranged to receive acoustic signals within a second ear canal opposing the first ear canal via a second earpiece of the binaural device representative of the second cranial attachment device 12.

In one non-limiting embodiment, control circuitry 70 is one of a processor and an ASIC circuitry. An input of acoustic transmitter 20 is connected to an output of signal generator 60. An output of acoustic receiver 30 is connected to an input of sampler 75, via optional filter 35. A first output of control circuitry 70 is connected to an input of signal generator 60, a second output of control circuitry 70 is connected to an input of memory 80 and a third output of control circuitry 70 is connected to display 90. Sampler 75 preferably comprises an A/D converter with a sampling frequency at least twice the sampling rate of the frequency output of signal generator 60, and further preferably has a sampling frequency at least twice the sampling rate of the frequencies of interest. In one non-limiting embodiment sampler 75 exhibits a sampling rate of 11 kHz. Sampler 75 is illustrated as part of computing platform 40, however this is not meant to be limiting in any way, and in one embodiment acoustic receiver 30 comprises therein sampler 75 and thus provides a digitized output for connection to control circuitry 70. The output of sampler 75 may be further directly connected to memory 80 without exceeding the scope. As described above, alternately optional filter 35 is placed between second cranial attachment device 12 and acoustic receiver 30, however this is not meant to be limiting in any way, and a combination of filters may be supplied without exceeding the scope. Additionally, a filter may be supplied between acoustic transmitter 20 and first cranial attachment device 11 without exceeding the scope.

In operation, first cranial attachment device 11 is to first cranial point 100 and second cranial attachment device 12 is attached to second cranial point 110. Signal generator 60 generates a signal, responsive to an output of control circuitry 70, and outputs the generated signal to acoustic transmitter 20. In one embodiment, the generated signal exhibits a single dominant frequency. In one embodiment, the single dominant frequency of the generated signal is less than 1000 Hz. In one further embodiment, the single dominant frequency of the generated signal is between 500 and 1000 Hz. In one further embodiment, the dominant frequency of the generated signal is between 550-700 Hz. In one yet further embodiment, the dominant frequency of the generated signal is between 600-650 Hz, and in one particular embodiment is 621 Hz. Acoustic transmitter 20 transforms the generated signal into an acoustic signal, and transmits the acoustic signal to first cranial point 100. Optionally, first tubular member 50 filters the transmitted acoustic signal removing acoustic artifacts. In one embodiment, the acoustic signal is continuously generated by signal generator 60, responsive to a first condition of the signal output by control circuitry 70, and interrupted by a second condition of the signal output by control circuitry 70. In one non-limiting embodiment transmission of the acoustic signal is for a period of 6 seconds, determining a measurement period. Measurement periods are preferably periodically performed on the patient, in one non-limiting embodiment exhibiting a period of 11 seconds.

Acoustic receiver 30 receives an acoustic signal from second cranial point 110. Advantageously, second tubular member 50 provides the filter action of optional filter 35 and thus filters the received acoustic signal removing any acoustic artifacts. The received acoustic signal comprises: the acoustic signal transmitted by acoustic transmitter 20 after traveling through patient head 120 and an acoustic signal representing the frequencies of various intracranial processes, particularly the vibration of the vascular system of the brain and the respiratory cycle. In one embodiment, vibration of the vascular system of the brain and of the respiratory cycle is transmitted by the material of second cranial attachment device 12 and second tubular member 50 to acoustic receiver 30. In one embodiment, the electrical representation of acoustic signal output by acoustic receiver 30 is filtered by optional filter 35, thus removing acoustic artifacts. The optionally filtered acoustic signal is sampled by sampler 75, and the samples are stored on memory 80. Alternately, optional filter 35 is implemented as a digital filter arranged to filter the output of sampler 75. In one embodiment, acoustic receiver 30 is arranged to continuously receive acoustic signals. Control circuitry 70 is arranged to determine a severity index of the condition of the patient and the ICP within patient head 120, as will be described below in relation to FIGS. 2A-2B. In one embodiment, as will be described below, the ICP is determined responsive to the severity index. The determined ICP and severity index are then displayed on display 90. In one embodiment, the determined ICP and severity index are further stored on memory 80.

Figure 2A:
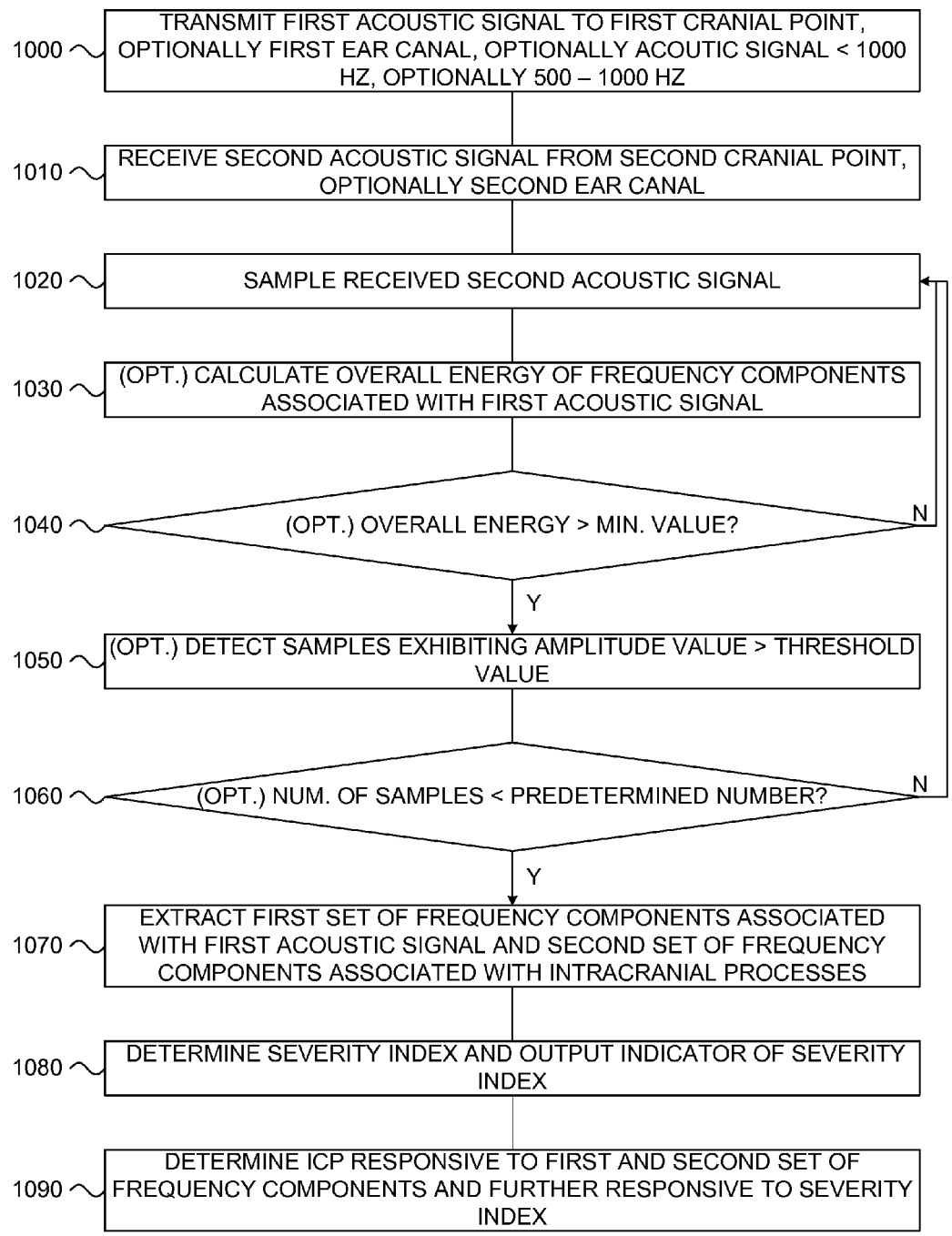
FIG. 2A illustrates a high level flow chart of a method for non-invasive measuring of ICP.

FIG. 2A illustrates a high level flow chart of a method of measuring intracranial pressure of a patient, automatically performed responsive to control circuitry 70 for each measurement period. In stage 1000, an acoustic signal is transmitted to a first cranial point. In one embodiment, the first cranial point is a first ear canal of the patient's head. In one embodiment, the transmitted acoustic signal exhibits a single dominant frequency. In one embodiment, the single dominant frequency of the transmitted acoustic signal is less than 1000 Hz. In one embodiment, the single dominant frequency of the transmitted acoustic signal is between 500 and 1000 Hz. In one embodiment, the acoustic signal is continuously transmitted. In stage 1010, an acoustic signal is received from a second cranial point. In one embodiment, the second cranial point is a second ear canal opposing the first ear canal. The received acoustic signal comprises: the transmitted acoustic signal of stage 1000 after traveling through the patient's head; and an acoustic signal representing the frequencies of intracranial processes, particularly the vibration of the vascular system of the brain and the respiratory cycle. In one embodiment, the signal is continuously received.

In stage 1020, the received signal of stage 1010 is sampled by sampler 75. In optional stage 1030, the overall energy of a set of frequency components associated with the transmitted acoustic signal of stage 1000 is calculated, in one embodiment by performing a Fast Fourier Transform. In optional stage 1040, the calculated overall energy of optional stage 1030 is compared to a predetermined minimum value to determine the quality of the transmitted signal of stage 1000 within the received signal of stage 1010. In one embodiment, the overall energy of the received signal of stage 1010 is calculated, the predetermined minimum value being a percentage of the calculated overall energy of the received signal of stage 1010. In one further embodiment, the percentage is about 66%. In another further embodiment, the calculated overall energy of the received signal is displayed, as will be described below in relation to FIG. 3. In the event the calculated overall energy is greater than the predetermined minimum value, or in the event that optional stages 1030-1040 are not performed, in optional stage 1050, samples of the received signal of stage 1010 exhibiting an amplitude value greater than a predetermined threshold value are detected, representing acoustic artifacts. In one embodiment, the predetermined threshold value is 95% of the maximum possible amplitude value of the received signal. In optional stage 1060, the number of detected samples of optional stage 1050 exhibiting an amplitude value greater than a predetermined threshold value are compared to a predetermined number to determine the quality of the received signal of stage 1010. In one embodiment, the predetermined number is 3% of the number of samples of the received signal of stage 1010.

In the event the number of detected samples is less than the predetermined number, or in the event that optional stages 1050-1060 are not performed, in stage 1070, a first set of frequency components associated with the transmitted signal of stage 1000 and a second set of frequency components associated with various intracranial processes are extracted from the received signal of stage 1010. In one embodiment, the first and second sets of frequency components are extracted by filtering the received signal with respective band pass filters. In one embodiment, the overall total energy of each of the first and second sets of frequency components are displayed, as will be described below in relation to FIG. 3.

In stage 1080, a severity index is determined, as will be described below in relation to stage 2040 of FIG. 2B. In one embodiment, an indicator of the determined severity index is output on the display, such as display 90. Alternatively, the determined severity index may be compared with a warning limit, and in the event that the determined severity index exceeds the warning limit, an emergency condition may be signaled to appropriate medical personnel, such as by lighting a warning light, activating an acoustic warning, or sending a signal to a network indicative of a medical emergency with a location identifier. In stage 1090, the ICP of the patient is determined responsive to the extracted first and second set of frequency components of stage 1070 and preferably further responsive to the determined severity index of stage 1080, as will be described further below in relation to stage 2050 of FIG. 2B. In one embodiment, the determined ICP is displayed on a display, such as display 90 of device 10.

In the event that in optional stage 1040 the calculated overall energy of the first set of frequency components is less than, or equal to, the predetermined minimum percentage, or in the event that in optional stage 1060 the number of detected samples is greater than, or equal to, the predetermined number, the sampled signal of stage 1020 is discarded and stage 1020 is again performed.

Figure 2B:
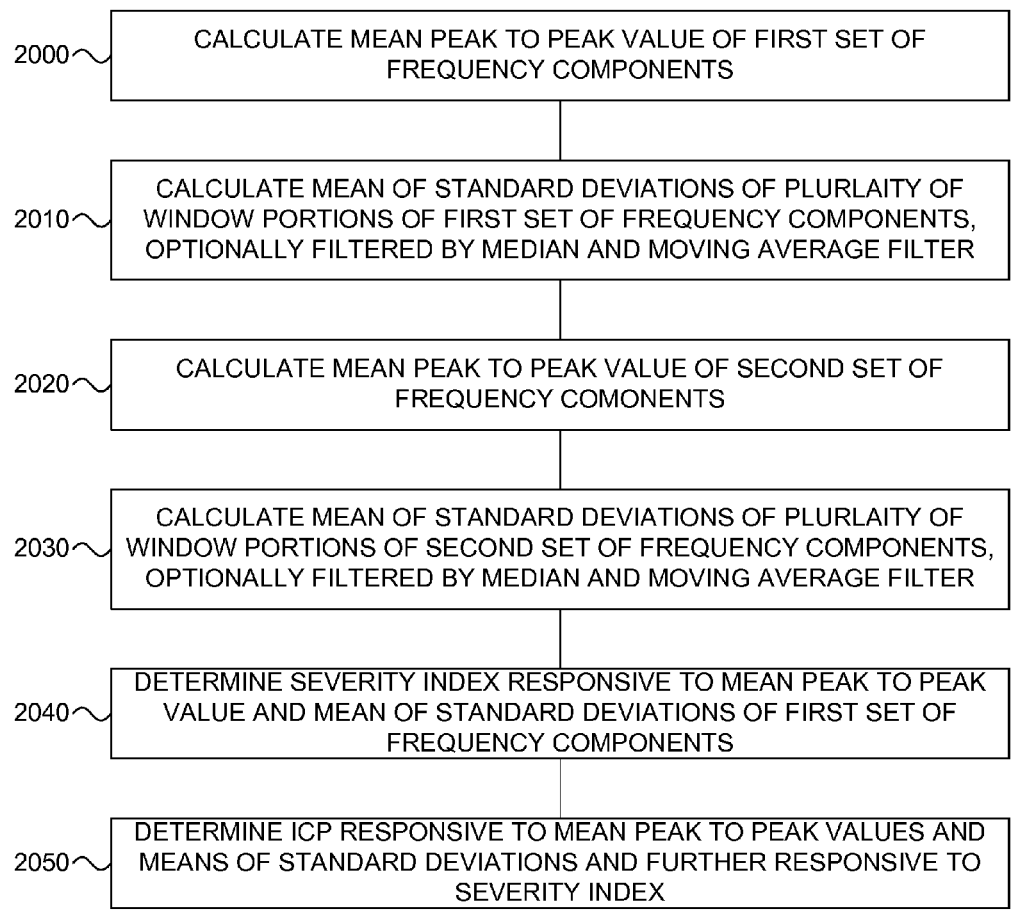
FIG. 2B illustrates a more detailed high level flow chart of the method of FIG. 2A.

FIG. 2B illustrates a high level flow chart describing in further detail a particular embodiment of stage 1080 and optional stage 1090 of FIG. 2A, all of the stages being optional. Specifically, stages 2000-2040 describe a particular embodiment of stage 1080 of FIG. 2A and stage 2050 describes a particular embodiment of stage 1090 of FIG. 2A. Alternatively, stages 2000-2030 and stage 2050 may be performed without stage 2040, thus implementing an embodiment of optional stage 1090 of FIG. 2A.

In stage 2000, an arithmetic mean of the peak to peak values of the amplitudes of the extracted first set of frequency components of stage 1070 is calculated. In one embodiment, the arithmetic mean is determined after adjusting the data set of stage 1070 to ignore peak to peak values of the amplitudes outside of a central range area of the extracted first set of frequency components. In one particular embodiment, 40% of the peak to peak values, exhibiting the lowest values, and 30% of the peak to peak values, exhibiting the highest values, are ignored. In one embodiment, the determined arithmetic mean is logarithmically adjusted. In one further embodiment, the adjusted arithmetic mean is mapped to a function. In one embodiment the function to be mapped to is a sigmoid function.

In stage 2010, the standard deviations of windowed portions of the extracted first set of frequency components of stage 1070 are calculated. In one embodiment, adjacent windowed portions at least partially overlap. In one further embodiment, the overlap portion is about 40% of the windowed portion. In one embodiment, the window is sized between 15 and 20 samples, and preferably 17 samples. The calculated standard deviations are in one embodiment filtered through a median filter. In one embodiment, the filtered standard deviations are further filtered through a moving average filter. An arithmetic mean of the standard deviations, optionally after being filtered through the median and moving average filter, is calculated. In one embodiment, the arithmetic mean is determined after adjusting the set of standard deviations to ignore standard deviation values outside of a central range area. In one particular embodiment, 40% of the standard deviation values, exhibiting the lowest values, and 30% of the standard deviation values, exhibiting the highest values, are ignored. In one embodiment, the determined arithmetic mean is logarithmically adjusted. In one further embodiment, the adjusted arithmetic mean is mapped to a function. In one embodiment the function to be mapped to is a sigmoid function.

In stage 2020, an arithmetic mean of the peak to peak values of the extracted second set of frequency components of stage 1070 is calculated. In one embodiment, the arithmetic mean is determined after adjusting the data set of stage 1070 to ignore peak to peak values of the amplitudes outside of a central range area of the extracted second set of frequency components. In one particular embodiment, 40% of the peak to peak values, exhibiting the lowest values, and 30% of the peak to peak values, exhibiting the highest values, are ignored. In one embodiment, the determined arithmetic mean is logarithmically adjusted. In one further embodiment, the adjusted arithmetic mean is to a function. In one embodiment the function to be mapped to is a sigmoid function.

In stage 2030, the standard deviations of windowed portions of the extracted second set of frequency components of stage 1070 are calculated. In one embodiment, adjacent windowed portions at least partially overlap. In one further embodiment, the overlap portion is about 40% of the windowed portion. In one embodiment, the window is sized between 15 and 20 samples, and preferably 17 samples. The calculated standard deviations are in one embodiment filtered through a median filter. In one embodiment, the filtered standard deviations are further filtered through a moving average filter. An arithmetic mean of the standard deviations, optionally after being filtered through the median and moving average filter, is calculated. In one embodiment, the arithmetic mean is determined after adjusting the set of standard deviations to ignore standard deviation values outside of a central range area. In one particular embodiment, 40% of the standard deviation values, exhibiting the lowest values, and 30% of the standard deviation values, exhibiting the highest values, are ignored. In one embodiment, the determined arithmetic mean is logarithmically adjusted. In one further embodiment, the adjusted arithmetic mean is to a function. In one embodiment the function to be mapped to is a sigmoid function.

In stage 2040, a severity index is determined. In one embodiment, the severity index comprises: the mathematical average of the calculated mean peak to peak value of the first set of frequency components of stage 2000 and the calculated mean of standard deviations of the first set of frequency components of stage 2010. In one embodiment, the severity index is adjusted utilizing a rounding factor. In one embodiment, the adjusted severity index is a whole number from 0 to 8.

In stage 2050, the ICP of the patient is determined. In one embodiment, the ICP comprises the arithmetic sum of: the calculated mean peak to peak values of stages 2000; the calculated mean peak to peak values of stage 2020; the calculated means of standard deviations of stage 2010; and the calculated means of standard deviations of stage 2030. In one embodiment, the determined ICP is mapped to a function. In one embodiment the function to be mapped to is a sigmoid function. In one further embodiment, the sigmoid function is given as:

$$F=1/(1+e^{-a(x-c)})$$ EQ. 1 where "x" is the determined ICP; "a" is the determined severity index of stage 2040 adjusted by a first adjustment value; and "c" is the determined severity index of stage 2040 adjusted by a second adjustment value. In one embodiment, the absolute values of the first adjustment value and the second adjustment value are equal, the first adjustment value and the second adjustment value exhibiting opposing signs. In one embodiment the first and second adjustment values are arithmetically respectively added to the determined severity index. In one embodiment, the absolute value of each of the first adjustment value and the second adjustment value is 5. In one embodiment, the determined ICP is further converted to units of millimeters of mercury by utilizing a scaling factor, preferably utilizing a rounding factor. In one embodiment, the arithmetic sum of the calculated mean peak to peak values of stage 2020 and the calculated means of the standard deviations, as described above in relation to stage 2030, represents an acoustic chaotic level and is displayed, as will be described below in relation to FIG. 3.

Figure 3:
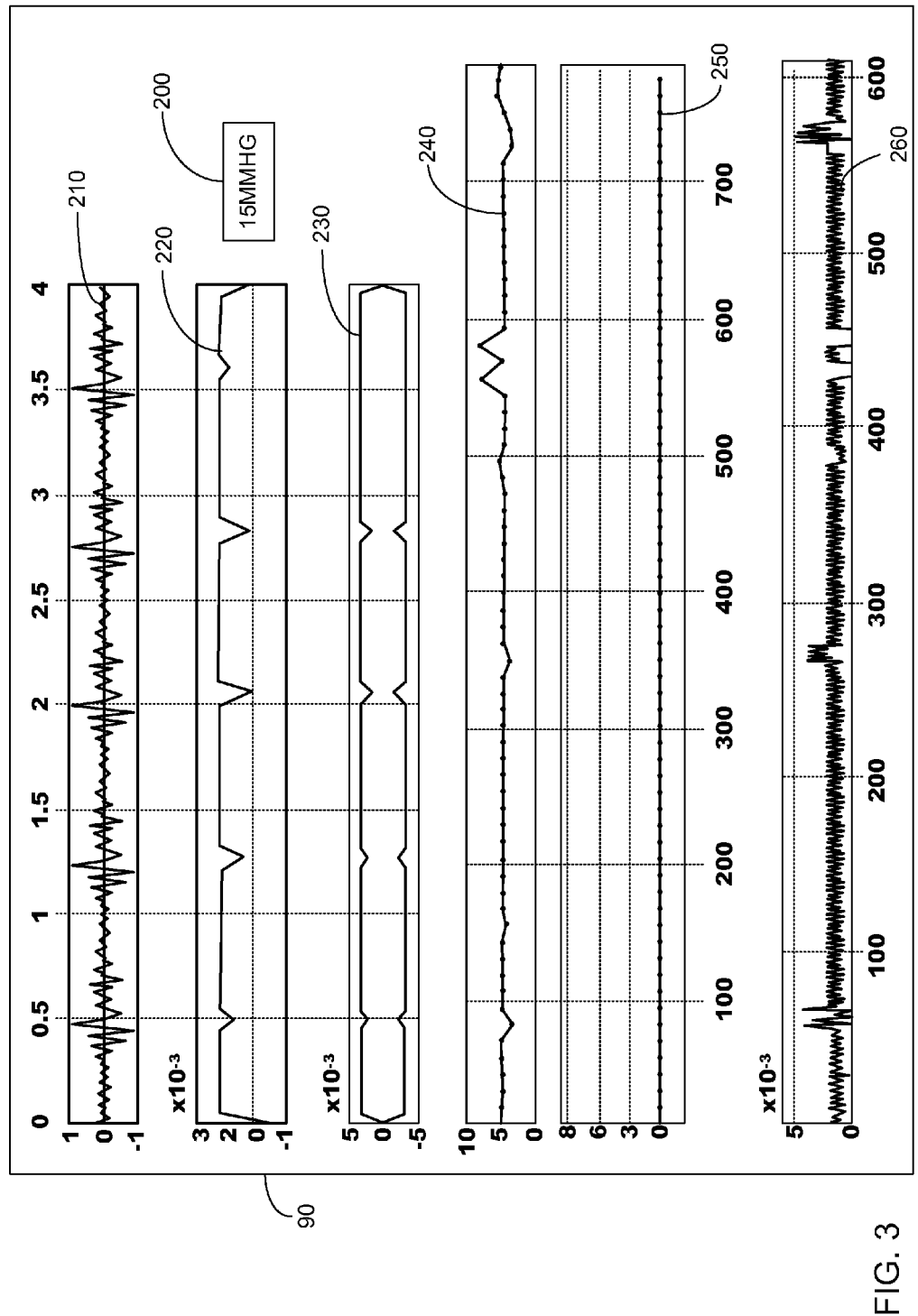
FIG. 3 illustrates a high level diagram of a display of the device of FIG. 1.

FIG. 3 illustrates a high level diagram of display 90 of FIG. 1. Section 200 of display 90 illustrates the current determined ICP in units of millimeters of mercury, as described above. Section 210 of display 90 illustrates a graph of the total acoustic energy of the acoustic signal received at acoustic receiver 30, as described above in relation to optional stage 1040 of FIG. 2A, where the x-axis represents time and the y-axis represents energy units in micro-watts. Section 220 of display 90 illustrates a graph of the total acoustic energy of the second set of frequency components of the received acoustic signal, associated with various intracranial processes, as described above in relation to stage 1070 of FIG. 2A, where the x-axis represents time and the y-axis represents energy units in micro-watts. Section 230 of display 90 illustrates a graph of the total acoustic energy of the first set of frequency components of the received acoustic signal, associated with the transmitted acoustic signal, as described above in relation to stage 1070 of FIG. 2A, where the x-axis represents time and the y-axis represents energy units in micro-watts.

Section 240 of display 90 illustrates a graph of the determined ICP values, where the x-axis represents time and the y-axis represents millimeters of mercury. Section 250 of display 90 illustrates a graph of the determined severity indexes, where the x-axis represents time and the y-axis represents levels of severity in whole numbers. In one embodiment, as described above, the levels of severity are numbered from 0 to 8. Changes in severity index over time can be easily noted, and are believed to be relevant to patient medical condition. Section 260 of display 90 illustrates a graph of the acoustic chaotic level, as described above in relation to stage 2050 of FIG. 2B, where the x-axis represents time and the y-axis represents levels of severity in whole numbers. In one embodiment, as described above, the levels of severity are numbered from 0 to 8.

Advantageously, each of the displayed graphs provides an indication of the medical condition of the patient, or information regarding the medical condition of the patient.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. In the claims of this application and in the description of the invention, except where the context requires otherwise due to express language or necessary implication, the word "comprise" or variations such as "comprises" or "comprising" is used in any inclusive sense, i.e. to specify the presence of the stated features but not to preclude the presence or addition of further features in various embodiments of the invention.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting. No admission is made that any reference constitutes prior art. The discussion of the reference states what their author's assert, and the applicants reserve the right to challenge the accuracy and pertinency of the cited documents. It will be clearly understood that, although a number of prior art complications are referred to herein, this reference does not constitute an admission that any of these documents forms part of the common general knowledge in the art in any country.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. An apparatus for measuring intracranial pressure comprising:
    a transmitter arranged to transmit a first acoustic signal through a first cranial point;
    a receiver arranged to receive a second acoustic signal from a second cranial point, the second acoustic signal comprising:
        the first acoustic signal after having traveled from the first cranial point to the second cranial point; and
        a third acoustic signal comprising acoustic vibrations of intracranial processes, and
    a control circuitry,
    wherein said control circuitry is arranged to:
        extract from said received second acoustic signal a first set of frequency components, said first set of frequency components associated with said transmitted first acoustic signal;
        extract from said received second acoustic signal a second set of frequency components, said second set of frequency components associated with the third acoustic signal;
        determine intracranial pressure responsive to said extracted first set of frequency components and said extracted second set of frequency components; and
        output said determined intracranial pressure.

2. The apparatus of claim 1, wherein the intracranial processes comprise the vascular system of the brain and the respiratory cycle.

3. The apparatus of claim 1, wherein said transmitted first acoustic signal exhibits a predetermined dominant frequency, said first set of frequency components comprising said predetermined dominant frequency, and
    wherein said second set of frequency components comprises frequencies of the acoustic vibrations of the intracranial processes.

4. The apparatus of claim 3, wherein said predetermined dominant frequency is 621 Hz.

5. The apparatus of claim 1, wherein said control circuitry is further arranged to:
    calculate a mean of peak to peak values of said extracted first set of frequency components;
    calculate a mean of standard deviations of a plurality of predetermined portions of said extracted first set of frequency components;
    calculate an average of said calculated first frequency component set peak to peak value mean and said calculated first frequency component set standard deviation mean;
    determine a severity index responsive to said calculated average; and
    output an indicator of said determined severity index.

6. The apparatus of claim 1, wherein said control circuitry is further arranged to:
    calculate a first function of a mean of peak to peak values of said extracted first set of frequency components;
    calculate a second function of a mean of standard deviations of a plurality of predetermined portions of said extracted first set of frequency components; and
    calculate a sum of said calculated first function and second function,
    wherein said determination of intracranial pressure by said control circuitry is responsive to said calculated sum.

7. The apparatus of claim 1, wherein said control circuitry is further arranged to:

calculate a third function of a mean of peak to peak values of said extracted second set of frequency components;
calculate a fourth function of a mean of standard deviations of a plurality of predetermined portions of said extracted second set of frequency components; and
calculate a sum of said calculated third function and fourth function,
wherein said determination of intracranial pressure by said control circuitry is responsive to said calculated sum.

8. The apparatus of claim 1, wherein said control circuitry is further arranged to:
calculate a first function of a mean of peak to peak values of said extracted first set of frequency components;
calculate a second function of a mean of standard deviations of a plurality of predetermined portions of said extracted first set of frequency components;
calculate a third function of a mean of peak to peak values of said extracted second set of frequency components;
calculate a fourth function of a mean of standard deviations of a plurality of predetermined portions of said extracted second set of frequency components; and
calculate a sum of said calculated first function, second function, third function and fourth function,
wherein said determination of intracranial pressure by said control circuitry is responsive to said calculated sum.

9. The apparatus of claim 1, wherein said control circuitry is further arranged to:
calculate a mean of peak to peak values of said extracted first set of frequency components;
calculate a first function of said first frequency component set peak to peak value mean;
calculate a mean of standard deviations of a plurality of predetermined portions of said extracted first set of frequency components;
calculate a second function of said first frequency component set standard deviation mean;
calculate an average of said calculated first frequency component set peak to peak value mean and said calculated first frequency component set standard deviation mean;
calculate a third function of a mean of peak to peak values of said extracted second set of frequency components;
calculate a fourth function of a mean of standard deviations of a plurality of predetermined portions of said extracted second set of frequency components,
determine a severity index responsive to said calculated average; and
calculate a sum of said calculated first function, second function, third function and fourth function,
wherein said determination of intracranial pressure by said control circuitry is responsive to said calculated sum and said determined severity index.

10. The apparatus of claim 1, wherein said control circuitry is further arranged to:
detect amplitude values of said received second acoustic signal greater than a predetermined threshold value, and
wherein said intracranial pressure is determined only in the event the number of said detected amplitude values is greater than a predetermined number.

11. A method for measuring intracranial pressure, the method comprising:
transmitting a first acoustic signal through a first cranial point;
receiving a second acoustic signal from a second cranial point, said received second acoustic signal comprising:
said transmitted first acoustic signal after having traveled from the first cranial point to the second cranial point; and
a third acoustic signal comprising acoustic vibrations of intracranial processes,
extracting from said received second acoustic signal a first set of frequency components, said first set of frequency components associated with said transmitted first acoustic signal;
extracting from said received second acoustic signal a second set of frequency components, said second set of frequency components associated with the third acoustic signal;
determining intracranial pressure responsive to said extracted first set of frequency components and said extracted second set of frequency components; and
outputting said determined intracranial pressure.

12. The method of claim 11, wherein the intracranial processes comprise the vascular system of the brain and the respiratory cycle.

13. The method of claim 11, wherein said transmitted first acoustic signal exhibits a predetermined dominant frequency, said first set of frequency components comprising said predetermined dominant frequency, and
wherein said second set of frequency components comprises frequencies of the acoustic vibrations of the intracranial processes.

14. The method of claim 13, wherein said predetermined dominant frequency is 621 Hz.

15. The method of claim 11, further comprising:
calculating a mean of peak to peak values of said extracted first set of frequency components;
calculating a mean of standard deviations of a plurality of predetermined portions of said extracted first set of frequency components;
calculating an average of said calculated first frequency component set peak to peak value mean and said calculated first frequency component set standard deviation mean;
determining a severity index responsive to said calculated average; and
outputting an indicator of said determined severity index.

16. The method of claim 11, further comprising:
calculating a first function of a mean of peak to peak values of said extracted first set of frequency components;
calculating a second function of a mean of standard deviations of a plurality of predetermined portions of said extracted first set of frequency components; and
calculating a sum of said calculated first function and second function,
wherein said determining intracranial pressure is responsive to said calculated SUM.

17. The method of claim 11, further comprising:
calculating a third function of a mean of peak to peak values of said extracted second set of frequency components;
calculating a fourth function of a mean of standard deviations of a plurality of predetermined portions of said extracted second set of frequency components; and
calculating a sum of said calculated third function and further function,
wherein said determining intracranial pressure is responsive to said calculated sum.

18. The method of claim 11, further comprising:
calculating a first function of a mean of peak to peak values of said extracted first set of frequency components;
calculating a second function of a mean of standard deviations of a plurality of predetermined portions of said extracted first set of frequency components;
calculating a third function of a mean of peak to peak values of said extracted second set of frequency components;
calculating a fourth function of a mean of standard deviations of a plurality of predetermined portions of said extracted second set of frequency components; and
calculating a sum of said calculated first function, second function, third function and fourth function,
wherein said determining intracranial pressure is responsive to said calculated SUM.

19. The method of claim 11, further comprising:
calculating a mean of peak to peak values of said extracted first set of frequency components;
calculating a first function of said first frequency component set peak to peak value mean;
calculating a mean of standard deviations of a plurality of predetermined portions of said extracted first set of frequency components;
calculating a second function of said first frequency component set standard deviation mean;
calculating an average of said calculated first frequency component set peak to peak value mean and said calculated first frequency component set standard deviation mean;
calculating a third function of a mean of peak to peak values of said extracted second set of frequency components;
calculating a fourth function of a mean of standard deviations of a plurality of predetermined portions of said extracted second set of frequency components,
determining a severity index responsive to said calculated average; and
calculating a sum of said calculated first function, second function, third function and fourth function,
wherein said determining intracranial pressure is responsive to said calculated sum and said determined severity index.

20. The method of claim 11, further comprising:
calculating the overall energy of the first set of frequency components,
wherein said determining intracranial pressure is only in the event said calculated overall energy of the first set of frequency components is greater than a predetermined minimum value.

* * * * *